United States Patent [19]

Naarding

[11] 4,084,433
[45] Apr. 18, 1978

[54] METHOD AND APPARATUS FOR QUANTITATIVELY AND QUALITATIVELY DETERMINING THE DUST CONTENT OF FIBROUS MATERIAL

[75] Inventor: Willem J. Naarding, Stad Delden, Netherlands

[73] Assignee: Hergeth KG Maschinenfabrik und Apparatebau, Dulmen, Germany

[21] Appl. No.: 728,055

[22] Filed: Sep. 30, 1976

[30] Foreign Application Priority Data

Oct. 4, 1975 Germany .............................. 2544563

[51] Int. Cl.² .............................................. G01N 5/00
[52] U.S. Cl. .................................................... 73/159
[58] Field of Search ...................... 73/159, 421 R, 424, 73/432 PS, 432 R, 433; 19/65 R, 107

[56] References Cited

U.S. PATENT DOCUMENTS

| 2,324,126 | 7/1943 | Anway | 73/159 |
| 2,910,731 | 11/1959 | Moore et al. | 19/65 R |
| 2,986,778 | 6/1961 | Goodwin et al. | 73/421 R X |
| 3,286,306 | 11/1966 | Brown | 73/159 |
| 3,545,281 | 12/1970 | Johnston | 73/433 |
| 3,987,517 | 10/1976 | Bonalumi | 19/107 |

Primary Examiner—Charles A. Ruehl
Attorney, Agent, or Firm—Diller, Brown, Ramik & Wight

[57] ABSTRACT

Method and apparatus for quantitatively and qualitatively determining the dust content of fibrous material, in which a representative sample of the fibrous material is opened to obtain individual fibers and release the dust contained therein. The individual fibers and fine dust are separated by a combination of gravity separation and air flow. Coarse dust is separated and collected incidental to the opening process. The dust quantity and quality are determined on a weight basis.

17 Claims, 4 Drawing Figures

METHOD AND APPARATUS FOR QUANTITATIVELY AND QUALITATIVELY DETERMINING THE DUST CONTENT OF FIBROUS MATERIAL

BACKGROUND OF THE INVENTION

This invention relates to a method of and apparatus for quantitatively and qualitatively determining the dust content released during opening of fibrous material, especially cotton, and especially fibrous material to be used in an open-end spinning process.

In an open-end spinning process, the dust content of the fibrous material plays a particular part, and in fact a decisive part in the carrying out of the open-end process. As is known, the opening of the fibrous material into individual fibers on the rotor releases fine dust, which reduces the yarn quality by blocking the collecting surface of the rotary spinning chamber, and can even lead to yarn breakage, or production loss resulting from cleaning operations.

In processing fibrous material it is of great importance to know the dust content of the sliver fed to the open-end spinning unit, and whether or not the sliver is suitable for spinning by an open-end process. Test apparatus used in conventional ring spinning processes, in which the fine dust content of the sliver does not play the same part as in an open-end process, is insufficient for an open-end process, as such apparatus separates only coarse dust and fibers. With the usual test apparatus, dust particles down to a granular size of 3 to 5 micrometers are accessible for measurement, whereas in fine dust which settles on the collecting surface of the rotary spinning chamber, there may be dust particles of 0.2 micrometers and less. A considerable part of the fine dust which causes production difficulties in an open-end spinning process is not caught by the previous test method, and these measurement results cannot be used successfully for an open-end spinning process.

Hitherto open-end spinning generally proceeded from the testing of a specific type of cotton on an open-end spinning unit to determine whether the spinning proceeds satisfactorily. This merely enabled it to be ascertained whether the particular type of cotton was suitable for the open-end spinning unit. No prediction was obtained regarding the quantitative and qualitative proportion of the dust. In addition, carrying out these tests on a production unit led in part to increased costs due to loss of time and production output.

BRIEF SUMMARY OF THE INVENTION

An object of the present invention is to provide a method of testing and apparatus for carrying out such testing which enables, using a relatively small or given amount of fibrous material or sliver from a large batch thereof, a sufficiently accurate quantitative and qualitative prediction of the content of dust inclusive of fine dust in the batch for assessment of the sliver spinnability in an open-end spinning process.

Basically, the present invention includes opening means adapted to receive a given amount or weight of fibrous material from a large batch which is to undergo open-end spinning. The opening means produces individual or opened fibers and releases the dust contained in the sample. The opened fibers and fine dust are separated and individually collected and weighed.

Coarse dust is collected separately from the individual fibers and fine dust.

The separation of individual fibers and fine dust is effected by discharging them through the mouth of a nozzle into an enclosed chamber. An air flow pattern is maintained in the chamber which allows the individual fibers to settle by gravity while the fine dust is entrained in the air flow.

In this way, it is possible to obtain reliable and predictable results from a small amount of fibrous material as regards the qualitative and quantitative dust content, which can be used for the spinning process on the production unit. Thus, the suitability of the fibrous material for an open-end spinning process may be ascertained in advance. The testing method may be carried out independently of a production unit, so that corresponding tests may be carried out continuously during production. The method of testing provides a secure basis for utilization of the results obtained thereby.

The test apparatus is advantageously constructed according to the invention in that a fiber opening device for the fibrous material discharges opened fibers and fine dust into a duct opening into a closed container, through which duct an airflow is passed in the direction of said container. Connected to the top of the container there is at least one vacuum pipe for air containing dust, said pipe being connected to a filter device for deposition and removal of the fine dust.

The apparatus is a test apparatus which is convenient and simple in construction. It enables single and series testing independently of the production process, e.g. in a textile laboratory, so that the continuing production by the open-end process can be supervised with relation to the quantitative and qualitative dust content of the fiber available for processing. Unsuitable fibrous material, i.e., material from which insufficient dust has been removed, can be withheld at the start from processing by the open-end method.

Advantageously, the duct leading from the fiber opening device into the container narrows into a nozzle shape in the direction of the airflow. Dependent upon the degree of constriction, there is a variation in the compression or concentration of the fibrous material, which has an effect on the subsequent reduction of pressure experienced by the fiber-fine dust mixture discharged into the chamber. There may be provided, in front of said duct, in the region of the opening roller and external to the container, a separation opening for coarse dust contained in the fibrous material, and for impurities, said opening discharging to a coarse dust collection bin. The container and the bin are suitably provided with air inlet openings, whose cross-sections may be regulated.

According to a further feature of the invention, the filter device for fine dust has a filter plate and a screen mesh, preferably a filter drum mounted in a screen drum, the drum being rotatably mounted. A nozzle advantageously serves to feed the fine dust-air mixture on to the filter. A nozzle or funnel may also be used for evacuation of the air from the screen drum. The said nozzles advantageously are in the shape of flat nozzles, and lie opposite each other respectively inside and outside the screen drum. This ensures that the fine dust can settle on the filter only on a strip extending parallel to the axis of the screen drum. As the screen drum is rotated slowly, a clean filter surface is continuously passed into the region between the nozzles, so that the flow and pressure conditions are kept constant during the testing period.

BRIEF DESCRIPTION OF THE DRAWING FIGURES

An embodiment of the invention will now be described, by way of example, with reference to the accompanying diagrammatic drawings, in which.

DETAILED DESCRIPTION OF THE INVENTION

Figure 1:
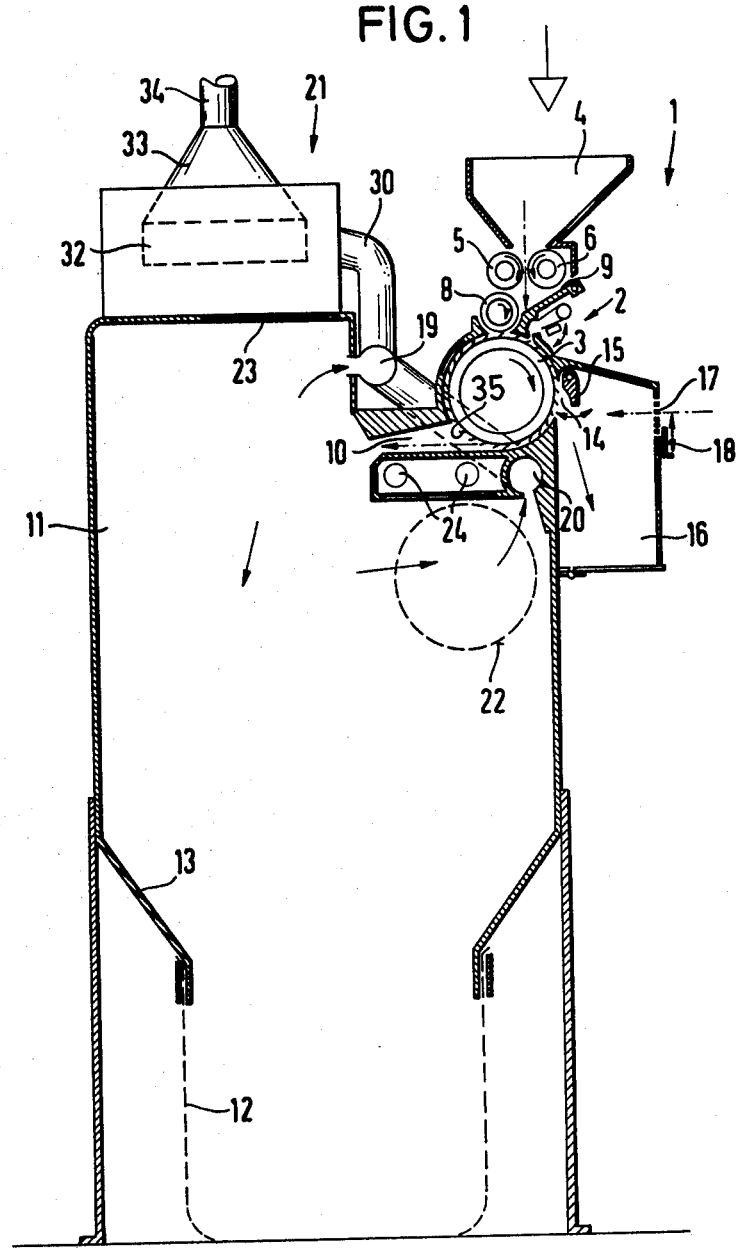
FIG. 1 is a sectional side view of apparatus for quantitative and qualitative determination of the dust content during opening of fibrous material according to the invention.
Figure 2:
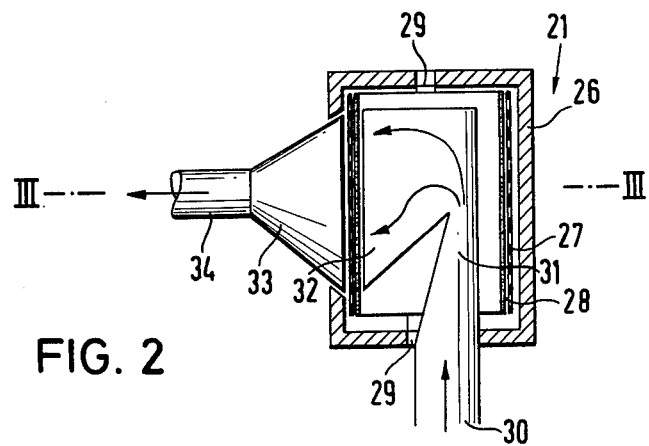
FIG. 2 is a cross sectional view of a screen drum filter, through which air is sucked, causing deposition of the dust, and having an arrangement of nozzles.
Figure 3:
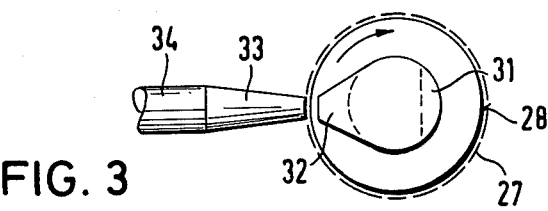
FIG. 3 is a section on the line III—III of FIG. 2.
Figure 4:
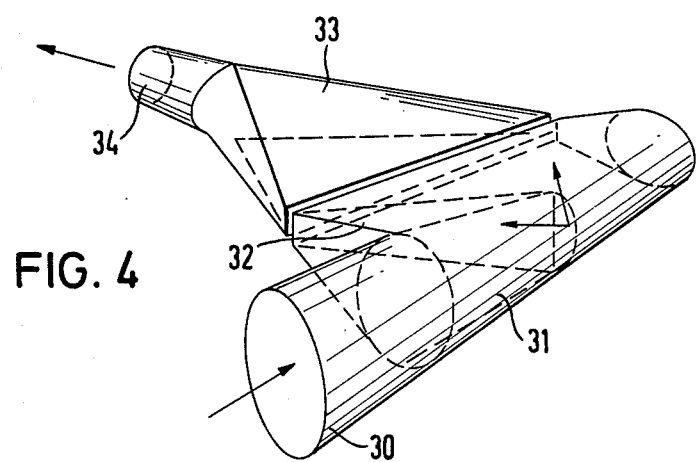
FIG. 4 is a perspective view showing the nozzle arrangement within the screen drum filter, omitting the screen drum casing.

Apparatus 1 for quantitative and qualitative determination of the dust content occurring during the opening of fibrous material has a fiber opening device 2, which can consist of one or more fiber opening rollers 3, which are preferably provided with teeth 35. The fibrous material is fed from a hopper 4 to two intake rollers 5 and 6. Mounted thereafter is a delivery roller 8 and a trough lever or pressure shoe 9. The fiber opening roller 3 rotates at a considerably higher speed than the delivery roller 8. Connected to the fiber opening device 2 and a roller device 3 there is a duct 10, which is preferably of outwardly tapering nozzle shape. Following the latter, there is a container 11, of relatively large volume, enabling perfect separation of dust and fibers. The container 11 defines an enclosed chamber into which the nozzle 10 discharges. At its bottom, the container 11 has a dust bag 12, removably attached to a hopper portion 13 thereof. The hopper portion 13 is designed so that the rectangular cross-section of the container 11 merges into a circular cross-section for the attachment of the dust bag 12.

In the region of the fiber opening roller 3, there is a separator opening 14 whose size may be regulated by flap 15. The separator opening 14 serves to separate coarse dust and impurities from the fibers as they are being loosened. Provided for this purpose there is a receptacle or bin 16, into which the impurities and the like can fall. The box 16 is provided with air inlet openings 17, whose cross-section may be regulated by means of slide 18, and these openings 17 are at the level of the opening 14. Suction pipes 19 and 20 lead from the container 11 to a screen drum filter assembly 21. One or more windows 22, 23 allow observation of the interior space of the container 11, and the interior of the container may be illuminated. Fluorescent tubes 24 may be provided for this purpose, illuminating the interior of the container to the side and downwards.

The screen drum filter assembly 21 has a casing 26, in which a screen drum 27 with a filter drum 28 mounted therein, are commonly rotatable around bearing axles 29. A suction pipe 30 leading from the suction pipes 19, 20 of the container 11, opens into a nozzle 31, extending into the interior of the screen drum, and connects with a nozzle portion 32 of flat construction, engaging behind the nozzle 31. The mouth of the nozzle portion 32 has opposite same a flat suction funnel or nozzle 33, to which a vacuum pipe 34 leading to a suction fan or the like (not shown) is connected.

The fibrous material to be tested is placed in the hopper 4 and passes therefrom between both the intake rollers 5,6 and the delivery mechanism 8,9 to the rapidly rotating opening roller 3, which opens the fibrous material into individual fibers. By means of the suction source connected to the pipe 34, the opened material is sucked through the nozzle-shaped duct 10 into the externally-closed container 11, the air gaining access through the openings 17 to the opening device 2 and the duct 10. As the fibrous material is opened, coarse dust and other impurities are separated at the separation opening 14 in the region of the periphery of the opening roller 3, and fall into receptacle 16. The opened fibers and fine dust are entrained in the airflow in the nozzle-shaped duct 10 and the individual fibers of the flowing stream are crowded together as they pass to the discharge mouth of the nozzle 10. When the stream emerges into the large space in the container 11, there is a sudden expansion of the stream which assures maximum separation of fibers and fine dust as they emerge from the duct 10 into the container 11. The fibers drop gravitationally onto the base of container 11 or into the catch device, i.e., into dust bag 12, whereas the freely-suspended fine dust is evacuated at the top of container 11 through the suction openings 19,20.

It will be appreciated that the pattern of air flow within the enclosed chamber is regulated so that whereas the individual fibers are free to settle toward the bottom of the chamber, the fine dust is entrained in the air flows to the opening 19 and 20.

The evacuated mixture of air and fine dust passes into the screen drum filter 21, where the fine dust can be deposited internally on the surface of the filter drum 28.

The dust-air mixture is preferably fed to the filter 28 through the nozzle 31, the air being removed directly through the funnel 33 located behind the screen drum surface. By means of the widening nozzle piece 32 engaging behind nozzle 31, the dust can settle on a strip of filter 28 extending parallel to the axis of the screen drum. The screen drum 27,28 is rotated slowly, so that a clean filter surface is continuously presented in the region between the jets 32,33. In this way any alteration in filter permeability which might occur after a short period is avoided, and the flow and pressure conditions are kept constant during the testing period.

The undercut shape of the flat nozzle piece 32 in front of filter 28 causes a distribution in the granular size of the fine dust extending parallel to the screen drum axis, large fine dust particles predominantly settling at the end of the filter 28, to which the airflow out of pipe 30 is least deflected.

By weighing the fibrous material inserted, the fibers in the bag 12, and the dust in receptacle 16 and in the screen drum filter 21, quantitative and qualitative values for the dust and microfine dust content of the tested fibrous material can be obtained. The values thus obtained then provide information as to whether and to what extent the batch of material to be processed and from which the tested sample was obtained is suitable for an open-end spinning process, or whether the fibrous material should first be subjected to a further cleaning process.

What is claimed is:

1. A method for determining the content of fine dust contained in a given amount of fibrous material, which fine dust is detrimental to open-end spinning, which comprises the steps of:

(a) opening said given amount of fibrous material to provide individual fibers and fine dust released therefrom;
(b) entraining the individual fibers and fine dust in a flow of air and subjecting the individual fibers and fine dust to constriction while thus entrained;
(c) separating said fine dust from said individual fibers;
(d) collecting said individual fibers;
(e) collecting said fine dust; and
(f) weighing the collected individual fibers and collected fine dust.

2. A method as defined in claim 1 wherein the separation of step (c) is effected by allowing said individual fibers to fall by gravity while said fine dust is entrained in an upwardly flowing stream of air.

3. A method as defined in claim 2 wherein the collection of fine dust of step (e) is effected by filtering said fine dust from said flowing stream of air.

4. A method as defined in claim 3 wherein the opening of step (a) is effected by toothed roller.

5. A method as defined in claim 1 including the step of separating coarse dust from said fibrous material as same is opened in step (a).

6. The method as defined in claim 1 including the step of expanding the air after the performance of step (b).

7. The method as defined in claim 6 wherein the expansion step is performed suddenly and immediately after the performance of step (b).

8. A method of quantitatively and qualitatively determining the dust content in a batch of fibrous material which is to be used for example in an open-end spinning process, which comprises the steps of:
(a) weighing a given mass of said batch of fibrous material;
(b) opening said given mass of fibrous material into individual fibers to release dust contained in said mass;
(c) creating a vacuum within an enclosed space by continuously withdrawing air from said enclosed space while allowing a limited amount of air to enter said enclosed space;
(d) entraining both said individual fibers and fine dust released therefrom in air entering said enclosed space and discharging same within said enclosed space so that said individual fibers are free to fall by gravity within said enclosed space;
(e) controlling the withdrawal of air of step (c) to entrain said fine dust in the air being withdrawn from said enclosed space while allowing said individual fibers to fall as in step (d);
(f) collecting said fine dust entrained in step (e);
(g) collecting said individual fibers which are separated by gravity in step (e); and
(h) weighing the collected fine dust and the collected individual fibers to obtain said quantitative and qualitative determination of dust content.

9. A method as defined in claim 8 wherein the individual fibers and fine dust entrained in step (d) are subjected to constricted air flow immediately prior to said discharge whereby said individual fibers and fine dust are compressed and then suddenly expanded.

10. Apparatus for determining the content of fine dust contained in a given amount of fibrous material, which fine dust is detrimental to open-end spinning, comprising the combination of opening means for opening said given amount of fibrous material to provide individual fibers and fine dust released therefrom, separating means for separating said fine dust from said individual fibers, collecting means for separately collecting said individual fibers and said fine dust, said separating means comprises a receptacle defining an enclosed space and having an inlet opening disposed below the top of said receptacle and an outlet opening disposed above said inlet opening, exhaust means for educting air from said enclosed space at a rate sufficient to entrain said fine dust, and a nozzle connected to said inlet opening and discharging inside said enclosed space.

11. Apparatus as defined in claim 10 wherein said opening means comprises a toothed roller and means for feeding said given amount of fibrous material to said roller, said roller discharging individual fibers and fine dust to said nozzle.

12. Apparatus as defined in claim 11 wherein said collecting means comprises a filter associated with said exhaust means for collecting said fine dust, said individual fibers being collected at the bottom of said receptacle.

13. Apparatus as defined in claim 12 wherein said filter is a drum filter, said exhaust means including a conduit leading from said outlet opening and terminating in a second nozzle discharging against the inner surface of said drum filter.

14. Apparatus as defined in claim 13 including means for rotating said drum filter.

15. Apparatus for qualitative and quantitative analysis of dust content contained in a batch of fibrous material containing fine dust which is detrimental to open-end spinning, comprising in combination:
a hollow receptacle defining an enclosed chamber and having an inlet opening and an outlet opening;
a nozzle within said chamber and leading from said inlet opening to present a discharge mouth below the level of said outlet opening;
opening means for opening the fibers of a sample of fibrous material from said batch and discharging individual fibers and fine dust released therefrom into said nozzle, whereby said individual fibers and fine dust are expelled from said discharge mouth within said chamber;
exhaust means connected to said outlet opening for continuously withdrawing air from said chamber at a rate sufficient to allow the discharged fibers to fall by gravity toward the bottom of said chamber while said fine dust is entrained in the air being withdrawn; and
filter means for collecting said entrained fine dust.

16. Apparatus as defined in claim 15 including a collecting bin adjacent said opening means and external to said chamber for collecting coarse dust released from said batch of fibrous material during opening thereof.

17. Apparatus as defined in claim 15 wherein at least two outlet openings are provided, one of which is located above the level of said discharge mouth and the other of which is located at a level below said discharge mouth.

* * * * *